United States Patent [19]

Maclachlan et al.

[11] Patent Number: 5,652,134

[45] Date of Patent: Jul. 29, 1997

[54] HYBRIDOMAS PRODUCING BLUETONGUE VIRUS-SPECIFIC MONOCLONALS

[75] Inventors: N. James Maclachlan, Davis, Calif.; Ginger M. Reddington; John J. Reddington, both of Wilton, Conn.

[73] Assignee: North Carolina State University, Raleigh, N.C.

[21] Appl. No.: 594,546

[22] Filed: Oct. 9, 1990

[51] Int. Cl.$^6$ .............. C12N 5/18; C07K 16/10; C12Q 1/70

[52] U.S. Cl. .............. 435/339; 530/388.3; 435/5

[58] Field of Search .............. 435/5, 70.2, 70.21, 435/172.2, 240.27, 235–238; 436/548; 530/387, 388.3

[56] References Cited

U.S. PATENT DOCUMENTS

| | | | |
|---|---|---|---|
| 4,873,189 | 10/1989 | Jochim et al. | 435/68 |
| 5,188,942 | 2/1993 | Reddington et al. | 435/28 |

OTHER PUBLICATIONS

Ausubel, F.M., et al., eds., *Current Protocols in Molecular Biology*, J. Wiley NY, v.2, suppl. 10, Unit 11.1.2. (1990).
Afshar, A., et al., J. Clin. Microbiol. 25: 1705–1710 (1987).
Callis, J.J., et al., *Illus. Man. for Recognition and Diagnosis of Certain Animal Diseases*, Mex. US Com. FM. Dis, Plum Island, 56–61 (1982).
Carter, P.B., et al., Vet. Clinics of North America: Small Small Animal Pract. 6: 1171–1179 (1986).
Guesdon, J.L., and Avrameas, S., Immunochemistry 14: 443–447 (1977).
Heidner, H.W., et al. J. Gen. Virol. 69: 2629–2636 (1988).
Jochim, M.M., in *Bluetongue and Related Orbiviruses*, Alan Liss pp. 423–433 (1985).
Jubb, K., et al., *Pathology of Domestic Animals*, v.2, Acad. Press pp. 108–112 (1985).
Lunt, R.A., et al., J. Gen Virol. 69: 2729–2740 (1988).
MacLachlan, et al., Am. J. Vet. Res. 45: 1469–1473 (1984).
MacLachlan, et al., Am. J. Vet. Res. 48 1031–1035 (1987).
Olsson, L., et al., J. Immunol. Methods 61: 17–32 (1983).
Ozawa, Y., in *Bluetongue and Related Orbiviruses* Alan Liss pp. 13–20 (1985).
Roy, P., Virus Research 13: 179–206 (1989).
Whetter, et al., J. Gen. Biol. 70: 1663–1676 (1989).

*Primary Examiner*—Marian C. Knode
*Assistant Examiner*—Donna C. Wortman
*Attorney, Agent, or Firm*—Bell, Seltzer, Park & Gibson

[57] ABSTRACT

Hybridomas producing monoclonal antibodies specific to Bluetongue virus are described. The antibodies are useful in rapid, competitive enzyme-linked immunosorbent assays (cELISAs) for the determination of Bluetongue virus antibodies in serum.

9 Claims, 1 Drawing Sheet

Figure 1. Schematic Drawing of How the Method Works test serum
+ bMAb

⊢_____⊣——BTV negative
(no Ab to BTV)

positive
(Ab to BTV)

bMAb
⊢_____⊣

Ab
⊢_____⊣

+ SA-HRPO

SA-HRPO
/
bMAb
⊢_____⊣

Ab
⊢_____⊣

+ HRPO chromogen
+ $H_2O_2$

SA-HRPO
/
bMAb    <u>Color</u>
⊢_____⊣

Ab    <u>No Color</u>
⊢_____⊣

HYBRIDOMAS PRODUCING BLUETONGUE VIRUS-SPECIFIC MONOCLONALS

BACKGROUND OF THE INVENTION

This invention relates to a rapid diagnostic test for the presence of Bluetongue vital specific antibody in serum. More particularly, the invention relates to a modified competitive enzyme linked immunosorbent assay for the detection in serum of the presence of Bluetongue viral specific antibody.

Bluetongue is an insect-borne disease of domestic (sheep, goats, cattle, water-buffaloes, camels, etc.) and wild (blesbok, white-tailed deer, elk, bighorn sheep, mule deer, pronghorn antelope, etc.) ruminants. In sheep and wild ruminants the disease is acute and the mortality is often high, whereas in cattle and goats the disease is usually milder.

First discovered a century ago and originally thought to be confined to Africa, confirmed outbreaks of Bluetongue virus have been reported in Europe, North and Latin America, and in the Near and Far East (Ozawa, Y., "Overview of the World Situation" in *Bluetongue and Related Orbiviruses*, Alan Liss, Inc., 1985, pages 13 to 20). Recent surveys indicate that Bluetongue virus is spreading silently to almost all the tropical and sub-tropical countries of the world (ibid., page 16).

In sheep the disease is characterized by fever, emaciation, oral lesions (often involving inflammation, ulceration, and necrosis of the tongue, lips and dental pads), and lameness (Callis, J. J., et al., *Illustrated Manual for the Recognition and Diagnosis of Certain Animal Diseases*, Mexico-United States Commission for the Prevention of Foot and Mouth Disease, 1982, pages 56 to 61). Focal hemorrhage may be present on the lips and gums, and the tongue may become edematous and congested or cyanotic, giving the disease its name. Morbidity is 80–100% in fully susceptible sheep; mortality is variable, from 0 to 50% (ibid., page 57).

Bluetongue is caused by a member of the genus Orbivirus (Reoviridae), commonly called Bluetongue virus or BTV. BTV is primarily transmitted by biting midges of the genus Culicoides. Infected cattle, which experience a prolonged viremia in contrast to sheep, provide a reservoir for the dissemination of the disease (Roy, P., 13 *Virus Research* 179–206 (1989)). Inapparent or latent infection may persist in cattle for a number of years, and recrudescence of the disease may be stimulated by the bites of Culicoides. Venereal transmission from an infected bull to a bred cow has also been demonstrated (Jubb, K. V. F., et al., *Pathology of Domestic Animals*, vol. 2, Academic Press, 1985, pages 108 to 112).

The diagnosis of Bluetongue generally involves either the isolation and identification of the virus or the detection of viral antigen-specific antibodies in serum (Jochim, M. M., "An Overview of Diagnostics for Bluetongue," *Bluetongue and Related Orbiviruses*, Alan Liss, Inc., 1985, pages 423 to 433). An example of the former type is described in U.S. Pat. No. 4,873,189 to Jochim and Jones (column 4, lines 42 to 59); virus from an infected animal isolated and adapted to grow in cell culture is complexed with BTV monoclonal antibody and identified in an indirect fluorescent antibody test. However, since serologic tests are easier and more economical to perform, they have been used more extensively than virus isolation to study the epizootiology of the disease.

The serology of Bluetongue is complicated by the identification of 24 different virus serotypes from different parts of the world, including five in North America (denoted serotypes 2, 10, 11, 13, and 17; see Roy, P., cited above, page 180). Although these may represent not so much distinct types as points on a spectrum of antigenicity brought about by reassortment of segmented orbivirus genomes (and, in fact, sequence analyses of BTV genomes have confirmed that all the genes representing the non-structural proteins of the virus as well as most of the inner capsid polypeptides are highly conserved, whereas the outer capsid polypeptides vary considerably; see Roy, P., cited above, at page 201), immunity to one serotype does not confer resistance against another and may cause "sensitization," with a more severe syndrome following infection by a second type (Judd, K. V. F., cited above, page 110). Moreover, epizootic hemorrhagic disease virus (EHDV), another orbivirus also spread by Culicoides midges (sometimes at the same time), is serologically related to BTV, and immunological cross-reactions between BTV and EHDV have been seen with a number of virus-specified proteins. Serological cross-reactions can hinder accurate diagnosis of BTV.

Serologic tests that have been developed to assay for antibodies have been recently reviewed (see the Jochim, M. M., chapter cited above, pages 427 to 431). These include complement fixation, immunodiffusion, immunofluorescence, hemolysis-in-gel and enzyme linked immunosorbent assay (ELISA). An agar gel immunodiffusion test is most widely used for detection of group-specific anti-BTV antibodies (Afshar, A., et al., *J. Clin. Microbiol.* 25:1705–1710 (1987)). However, the test is not highly sensitive, specific, or quantitative, and interpretation of the results is often subjective.

As an alternative, several ELISAs have been developed. The first suggested was an indirect (or I-) ELISA (see Afshar, et al., cited above, and Lunt, R. A., et al., *J. Gen. Virol.* 69:2729–2740 (1988)). In this procedure, multiple wells on microtiter plates are coated with BTV antigen by passive adsorption for 18 hours, then washed and incubated with test sera for 3 hours, then washed and incubated with horseradish peroxidase (HRPO) labelled with antibovine IgG or antiovine IgG for an hour, and then incubated with an HRPO chromogenic substrate and hydrogen peroxide ($H_2O_2$) for 30 minutes; the appearance of color (read as an optical density value at a wavelength appropriate for the HRPO-oxidized chromogen) is read as a negative result (Afshar, et al. cited above, page 1706).

The test was described as being reliable, but it failed to detect early postinfection reactions of experimentally infected animals (*ibid.*). Moreover, problems with cross-reactivity with other orbiviruses were encountered (Lunt, et al., cited above). To circumvent these problems, a competitive (or c-) ELISA was developed. This method was similar to the I-ELISA except that test serum was incubated with monoclonal antibody for 3 hours in the second step; the IgG labelled-HRPO and HRPO substrate incubations were the same (Afshar, et al., cited above, page 1706).

This test was subsequently modified in a blocking (B-) ELISA, which replaced the three-hour serum/antibody/antigen incubation (second step) with three one-hour incubations: an incubation of serum with antigen followed by an incubation with added monoclonal antibody followed by an incubation with added IgG labelled-HRPO (Lunt, et al., cited above).

Cross-reactivity with other orbiviruses continued to plague the results, however. Animals which had undergone separate infections with both BTV and EHVD and animals from regions of high orbivirus activity exhibited anomalous titers (*ibid.*). Moreover, no assessment was made of immunological responses from mouse-derived components inherent in a procedure involving mouse brain-adapted virus, which may have interfered non-specifically in the assay.

SUMMARY OF THE INVENTION

It is an object of the present invention to provide a new, accurate, sensitive, and reliable method for determining antibodies to Bluetongue virus in serum. It is a further object of the present invention to provide a modified competitive enzyme immunosorbent assay (cELISA) for Bluetongue virus antibodies in serum that is simpler and faster than previously described ELISAs.

These and other objects are accomplished by the present invention, which describes an improvement in an ELISA method for determining Bluetongue virus specific antibodies in serum. This invention, in its preferred embodiments, utilizes the avidin-biotin system and involves the use of biotinylated antibodies in conjunction with enzyme conjugates of avidin. Serum antibodies are determined in the preferred embodiment by incubating the serum with Bluetongue virus antigen and employing a biotinylated antibody with an avidin-enzyme complex to compete with serum antibody for the virus antigen binding sites, or to assay for serum antibody binding sites.

This invention encompasses biotinylated antibody to Bluetongue virus and biotinylated antibody to Bluetongue virus specific monoclonal antibody. Thus, typical assay procedures require two or three steps. The antigen may be first incubated with antigen-specific biotinylated primary antibody, and then with an avidin-enzyme complex. In another embodiment, antigen, biotinylated monoclonal antibody, and an avidin enzyme complex are incubated together instead of sequentially. Alternatively, an unlabelled primary antibody may be used, followed by sequential incubations with a species-specific biotinylated anti-immunoglobulin and an avidin enzyme complex. Alternatively, enzyme may be conjugated directly to the monoclonal.

Preferred biotinylated antibodies of this invention are relatively homogeneous monoclonal antibodies. Preferred avidin-enzyme complexes utilize carbohydrate-free, nearly neutral streptavidin. One preferred enzyme conjugate is peroxidase, which has a variety of chromogenic substrates having colored, easily measured products.

In an example assay, streptavidin-horseradish peroxidase and synthetic substrate are used with biotinylated monoclonal antibody to Bluetongue virus. Briefly described, test tubes or wells of a microtiter plate coated with inactivated BTV as antigen are incubated with test serum and biotinylated monoclonal antibody for one hour. The plate is washed, removing the unbound antibody; if antibodies are present in the test serum samples, they inhibit the binding of the biotinylated monoclonal to the virus. Streptavidin linked to horseradish peroxidase is added and incubated for half an hour; the avidin protein moiety binds to the biotin ligand conjugated to the monoclonal in samples where the monoclonal is attached to antigen. Unbound streptavidin-horseradish peroxidase is washed away, and a peroxidase chromogenic substrate and hydrogen peroxide are added and incubated for ten minutes to an hour. The reaction is stopped, and the appearance of color shows an absence of antibody in the test serum. This results because, in the absence of test serum antibody, the biotinylated antibody was able to bind to the virus, which in turn allowed the binding of the enzyme linked ligand to the monoclonal.

The procedure may be shortened by combining incubation steps. Thus, antigen, serum, and streptavidin-horseradish peroxidase may be incubated simultaneously prior to assaying for peroxidase as described above.

BRIEF DESCRIPTION OF THE FIGURE

The diagnostic test of this invention is schematically illustrated in FIG. 1. Diluted test serum, along with biotinylated monoclonal antibody (bMAb), is pipetted into a microtiter plate well sketched as ⌐——┘ coated with inactivated Bluetongue virus (BTV). If antibodies (Ab) are present in the test serum, they bind to the virus and prohibit the binding of the bMAb; if antibodies are not present, the bMAb binds to the virus. The plate is washed, and streptavidin-tagged horseradish peroxidase is added (SA-HRPO). The avidin moiety binds to the biotin ligands that have attached to the monoclonal. The plate is washed, removing unbound peroxidase. A chromogenic horseradish peroxidase substrate (HRPO chromogen) and hydrogen peroxide ($H_2O_2$) are added. If present, the peroxidase oxidizes its substrate to yield a colored product.

Thus, an appearance of color in a well at the end of the test shows the presence of avidin-bound peroxidase attached to the monoclonal, and, thus, an absence of Bluetongue virus-specific antibodies in the test serum. The color change is proportional to the amount of monoclonal that bound to the virus. An absence of color, on the other hand, shows the presence of Bluetongue virus-specific antibodies in the serum, which bound to the virus and inhibited the attachment of the monoclonal and, consequently, the enzyme.

DETAILED DESCRIPTION OF THE INVENTION

This invention describes a diagnostic test for determining the presence of antibodies to the Bluetongue virus in serum samples from animals in an unknown state of infection. The method is a modified competitive Enzyme Linked Immunosorbent Assay (cELISA), and utilizes either a biotinylated monoclonal antibody in conjunction with streptavidin-enzyme and synthetic substrate, or enzyme-conjugated monoclonal and synthetic substrate to detect antibodies specific for the Bluetongue virus (BTV).

Test serum is incubated with Bluetongue virus antigen. If the serum contains antibodies to Bluetongue virus, the antibodies adhere to the antigen. The antigen is also exposed to tagged monoclonal antibodies to Bluetongue virus. If previously unexposed to BTV antibodies, the antigen readily attaches the tagged antibodies. On the other hand, it does not react if it has antibodies from the test serum adherent. The tag may be either an enzyme, or a group that binds an enzyme to secure it. Subsequent measurement of enzyme activity estimates how much tagged antibody is present and bound to antigen unexposed to Bluetongue virus-specific antibodies in the test serum. From that, by difference, amounts of antibody in the original test sample can be calculated.

A BTV antigen is employed in the test. By a "BTV antigen" is meant any substance which is capable, under appropriate conditions, of inducing a specific immune response to Bluetongue virus and of reacting with the products of that response, that is, with specific antibodies or specifically sensitized T-lymphocytes, or both. By Bluetongue virus (BTV) is meant any serotype of the Bluetongue orbivirus disease of sheep, cattle, goats and wild ruminants. Live viruses, inactivated (e.g., irradiated, frozen, psoral-treated, formalin-treated) viruses, lysed viruses, and coat proteins (either isolated and purified, or expressed in transformed or transfected cell lines) may be used as BTV antigens. Preferred BTV antigens are immunologically group specific, inactivated viruses.

An antibody to the BTV antigen is also employed. By "antibody" is meant an immunoglobulin having a specific amino acid sequence by virtue of which it interacts with a BTV antigen that induced its synthesis in cells of the lymphoid series, or with an antigen closely related to it. Any BTV-specific antibody may be employed, but monoclonal antibodies are preferred. By "monoclonal" is meant derived from a single cell or pertaining to a single clone.

As described above, the antibody is tagged with either an enzyme or a marker that will conjugate with an enzyme, so that the enzyme activity can be measured in the assay. Any marker used in the art may be used for this purpose. A biotinylated antibody is preferred. By "biotinylated" is meant an antibody labelled with conjugated biotin, whose high affinity for avidin or anti-biotin antibodies is exploited by those skilled in the art to mark the spot to which an antibody binds by direct immunoassay. Any form of biotin, its ester or other derivative may be used. Nonlimiting examples are NHS-biotin and NHS-LC-biotin.

Alternatively, a second antibody that will react with the BTV antibody may be tagged with biotin. In this embodiment, an extra step is added to the reaction sequence. After incubation of BTV-specific monoclonal antibody with antigen, the samples are washed to remove unbound monoclonal. Then a biotinylated antibody reactive to the BTV-specific monoclonal is added prior to washing and adding enzyme. Afterwards, an enzyme bearing a group that will bind to the biotin flags the situs of the two attached antibodies. For example, where the BTV-specific monoclonal is prepared from a mouse hydridoma, a biotinylated rabbit anti-mouse antibody can be used to mark the spot where BTV-specific monoclonal has bound.

Alternatively, the BTV-specific monoclonal may be conjugated directly with enzyme, which is itself the tag. In principle like other embodiments described above, test sera incubated with this type of tagged monoclonal binds it if no BTV virus-specific antibodies are present. Assay for enzyme activity can be used then to identify samples showing no measurable amounts of BTV-specific antibody.

An enzyme that is a tag or that bears a group that will bind with the tag on the antibody is employed. Any enzyme may be used for this purpose, including, but not limited to, horseradish or any other peroxidase, alkaline phosphatase, beta-galactosidase, urease and the like. Because of its ready accessibility and fast color development with chromogenic substrates, horseradish peroxidase is preferred.

An enzyme substrate is employed to detect enzyme activity, and, thereby, the location of the tag. By "substrate" is meant a substance upon which an enzyme acts. Preferred substrates are well known to those skilled in the art and are easily measurable, for example, by viewing color development in comparison with standards or by reading optical densities at appropriate wavelengths; some substrates yield products easily measured. Most preferred substrates are chromophoric or yield chromophoric products, so that enzyme activity can be readily measured by the appearance or disappearance of color. Examples of enzyme substrates include p-nitrophenyl phosphate for alkaline phosphatase, bromocresol purple and urea for urease, p-nitrophenyl-beta-galactopyranoside for beta-galactosidase, and the like. Horseradish peroxidase requires hydrogen peroxide in addition to another substrate that serves as a hydrogen donor including, for example, 2,2'-azino-bis(3-ethylbenzthiazoline-6-sulfonic acid) (hereinafter referred to as ABTS), 5-aminosalicylic acid, o-diaminobenzidine, 3,3'-dimethoxybenzidine, o-phenylenediamine (free base or dihydrochloride), 3,3',5,5'-tetramethylbenzidine (base or dihydrochloride), and the like chromogens.

The enzyme bears a group that will bind to the tag on the BTV-specific monoclonal or an antibody attached to it. Where the antibody is tagged with biotin, avidin may be employed. Avidin is a protein-carbohydrate complex in egg white that interacts with biotin. However, sometimes avidin's basic isoelectric point causes greater electrostatic interactions yielding a higher background, and the carbohydrate portion binds lectin-like proteins in animal tissue. To circumvent these problems, streptavidin is preferred. Streptavidin is an extracelluIlar protein of *Streptomyces avidinii* which is very similar to avidin, having a molecular weight of 60,000 daltons and consisting of 4 identical subunits, each containing a single biotin-binding site. Moreover, it has a near neutral charge under physiological conditions and is free of carbohydrate side chains.

In the practice of this invention, test serum is compared with positive serum (from animals infected with BTV) and negative serum (from animals uninfected with BTV) as comparisons and controls. Sera and/or buffer-diluted sera are spotted out on microtiter plates or immunoblots having BTV antigen, and biotinylated antibody is added to all the samples and incubated so that antigen may bind with test antibodies or biotinylated antibody. Following another buffered wash, horseradish peroxidase labelled with streptavidin is introduced to all the samples. After an appropriate incubation period (e.g., one half hour) and another buffered wash, ABTS and hydrogen peroxide are added. The reaction is stopped using a sodium dodecyl sulfate buffer after the ABTS chromophoric product has developed in the negative sera (e.g., in 10 minutes to half an hour). Color is then read as an absorbance reading at 410 nanometers or by comparison with a standard.

The assay method may be modified by incubating sera with BTV antigen and incubating prior to adding biotinylated antibody and proceeding as outlined above. Alternatively, the serum may be incubated with both BTV-specific monoclonal antibody and streptavidin-horseradish peroxidase prior to incubation for 15 minutes to an hour, washing, and then adding ABTS and hydrogen peroxide and proceeding as outlined above. Alternatively, antigen may be coated on magnetic beads, plastic sticks, nitrocellulose, or the like instead of test tubes or microtiter plate wells. Other horseradish peroxidase substrates may be employed. These and other variations on ELISA protocols known by those skilled in the art are encompassed by this invention, and several specific illustrations of such methods are illustrated in the Examples below.

EXAMPLES

The following examples are presented to further illustrate and explain the present invention and should not be taken as limiting in any regard. Unless otherwise indicated, all parts and percentages are by weight, and are based on the weight at the particular stage of the processing being described.

EXAMPLE 1

This example gives procedures for preparation of the standard sera and reagents that may be used in the diagnostic test described in Example 2.

Preparation of Bovine Antisera to Bluetongue Virus. A positive serum to use as reference standard (positive control) is prepared in this section.

A colostrum-deprived calf is raised in insect-secure isolation facilities from birth until all sera had been collected (9 to 10 months). Immunoglobulin (IgG) is not detected (using a radial immunodiffusion assay kit, VMRD, Pullman, Wash.) in serum from this calf within 24 hours of birth, confirming that passive transfer of maternal immunity had not occurred.

The calf is given antibiotics for 4 weeks after birth. At 5 weeks of age, the calf is intraveneously inoculated with $10^{6.5}$ TCID$_{50}$ of Bluetongue virus (BTV) serotype 13. Nineteen weeks later, the calf is inoculated IV with $10^{6.3}$ TCID$_{50}$ of BTV serotype 10. Serum collected from this calf at 10 weeks after the second inoculation is used as a positive control, and shows antibodies to Bluetongue virus using agargel immunodiffusion, serum neutralization and competitive ELISA procedures. The calf remains in perfect health throughout the study period.

Preparation of Negative Bovine Serum. A negative serum for use as a control is prepared in this section.

Another colostrum-deprived calf is raised in insect-secure isolation facilities as described above. Serum collected from this animal at approximately 12 to 15 months of age is used as a negative control. The animal remains in perfect health throughout the study period.

Preparation of BTV Antigen. Serotype 10 Bluetongue virus (hereinafter referred to as BTV-10) isolated in 1953 and originally designated CA-8 is subsequently passaged in sheep (three times), embryonating chicken eggs (twice), primary lamb kidney (seven times), and in baby hamster kidney (BHK-21 cells) (three times) as previously described (MacLachlan, et al., Am. J. Vet. Res. 45:1469–1473 (1984) and Heidner, et al., J. Gen. Virol. 69:2629–2636 (1988)). Virus is successively plaque-picked seven times from agar-overlaid Vero cells and stock cultures are then propagated in BHK-21 cells.

Confluent T-75 flasks of BHK-21 cells are grown in minimum essential medium (MEM) with 10% fetal bovine serum, 10/5 tryptose phosphate broth, and 1% penicillin/streptomycin. The cells are then infected with BTV-10 at a multiplicity of infection of 0.5 (viral stock titer is $10^{10.6}$ TCID$_{50}$/ml) in a volume of 3.5 ml of MEM and incubated for 30 minutes at 37° C. Seventeen ml more of complete media are then added. Twenty-four hours later, the cells are washed three times with phosphate buffered saline (PBS) and 10 ml of 10% lactose monohydrate in 0.1M NaHPO$_4$, pH 8.0, are added to each flask. The flasks and their contents are quick frozen at −70° C. before being rapidly thawed in warm water. The protein concentration is determined, and the lysed cell-virus mixture protein concentration adjusted to 200 ug/ml in 0.1M NaHCO$_3$, pH 8.0. The virus in the protein-virus mixture is then inactivated by means of irradiation.

Monoclonal Antibody Preparation. BALB/c mice are inoculated intravenously with the BTV-10 stock as previously described (Heidner, et al., cited above). Mice are resensitized 1 month later with 1.0 ml of a 50% (v/v) suspension of infected mouse brains (prepared from the brains of suckling mice inoculated intracranially with stock challenge BTV-10) in Freund's complete adjuvant, administered subcutaneously at four separate sites. Subcutaneous injections at two sites are repeated with 0.5 ml 50% (v/v) suckling mouse brain suspension in Freund's complete adjuvant 2 weeks later. Mice are intravenously inoculated with stock challenge virus 3 days before fusion.

Fusion of splenic lymphocytes with cells from the American Type Culture Collection (hereinafter referred to as A.T.C.C.) P3-X63-Ag8.653 myeloma line is carried out in the presence of polyethylene glycol (in a M$_r$, molecular weight ratio, of 1450) in RPMI (Roswell Park Memorial Institute) 1640 medium. Hybridomas are selected by growth on 96-well culture plates in hypoxanthine, aminopterin, and thymidine medium containing 20% fetal bovine serum. Hybridomas may also be grown in tissue culture, e.g., spinner flasks or bioreactors.

Hybridomas producing neutralizing antibodies are selected with a microneutralization test with BHK-21 cells and BTV-10. Appropriate hydridomas are cloned at least three times by limiting dilution employing procedures used by the hybridoma facility of the College of Veterinary Medicine, North Carolina State University (published in Carter, et al., Vet. Clinics of North America: Small Animal Pract. 6:1171–1179 (1986)). The hybridomas encoding the monoclonal antibody employed in this invention, designated BTV 035 for monoclonal 035 (MAb 035) and BTV 290 for monoclonal 290 (MAb 290), were deposited in the A.T.C.C., 12301 Parklawn Drive, Rockville, Md. 20852, on Sep. 28, 1990, and bear A.T.C.C. accession numbers HB 10567 for MAb 290 and HB 10568 for MAb 035, respectively.

High titer ascitic fluid from each of the hydridomas is produced in BALB/c mice. The mice are primed by a 0.5 ml intraperitoneally injected bolus of Pristene (2,6,10,14-tetramethylpentadecane). The monoclonal antibodies are isolated from the ascitic fluid by first cutting the fluid with a 50% (v/v) solution of saturated ammonium sulfate overnight at 4° C. The precipitate is then dialyzed extensively against PBS.

The protein specificity of the monoclonal antibodies are determined by immunoprecipitation of ($^{35}$S)-methionine labelled ultracentrifuged lysates of BTV-infected BHK-21 cells as described by Whetter, et al., J. Gen. Virol. 70:1663–1676 (1989). Proteins are resolved on a 10% polyacrylamide gel and identified by comparison to ($^{35}$S)-methionine-labelled proteins in density gradient purified BTV, and those proteins precipitated from BTV-infected BHK-21 cell lysates by a hyperimmune rabbit antiserum to BTV-10. The electrophoretic mobility of the immunoprecipitated proteins are compared to that of M$_r$ markers to determine their size and identity (MacLachlan, et al., Am. J. Vet. Res. 48:1031–1035 (1987)).

Specificity of monoclonal antibodies are confirmed with a blocking procedure. Preincubation of the antibody with either gradient-purified BTV or BTV-infected BHK-21 cell lysate prior to indirect immunofluorescent staining of BTV-infected monolayers of Vero cells abolishes all staining, whereas preincubation of the antibody with mock-infected BHK-21 cell lysate did not block immunofluorescent staining. Furthermore, fluorescein isothiocyanate-conjugated monoclonal antibody stains monolayers of Vero cells infected with any one of the U.S. serotypes of BTV (serotypes 2, 10, 11, 13, 17), whereas the antibody does not stain uninfected Vero cells or monolayers of Vero cells infected with epizootic hemorragic disease virus serotypes 1 or 2. Similarly, the antibody does not precipitate any proteins from ($^{35}$S)-methionine labelled proteins in mock infected lysates of BHK-21.

Using the cELISA described in the next Example, both MAb 035 and MAb 290 react with all 24 BTV serotypes. With many antisera, MAb 035 was inhibited to a greater extent than was MAb 290, indicating that MAb is more specific. Competitive binding assays show that both monoclonal antibodies react to different, specific epitopes on the vital structural protein VP-7. Both monoclonals are of the IgG$_{2a}$ class.

Biotinylated Monoclonal Antibody Preparation. For methods employing biotinylated antibody, the antibodies described above are biotinylated using a commercially available kit (Pierce Chemical), according to the manufacturer's instructions. Briefly, 20 mg of the monoclonal IgG is dissolved in 1 ml of 50 mM bicarbonate buffer, pH 8.5. A N-hydroxysuccinimide long chain ester of biotin, 0.4 mg, is then added and the solution incubated for 2 hours on ice. Unreacted biotin is removed by centrifugation of the product at 1000 x g for 30 minutes using a Centicon-30 Microconcentrator from Amicon. After centrifugation, the sample is diluted in 0.1M phosphate buffer, pH 7 0. This process is repeated two more times before being stored at −20° C.

EXAMPLE 2

This example describes a modified cELISA assay for detecting Bluetongue virus-specific antibodies in serum according to the invention.

Test tubes or a 96-well microtiter plate is coated with the antigen described in Example 1 at a concentration of 200 ug of crude cellular protein per ml of coating buffer (0.1 M $NaHCO_3$ buffer, pH 8.0). The antigen is allowed to bind for 24 hours at 4° C. before being dried at room temperature for 4 hours in a laminar flow hood. (Once dry, the plates may be placed in Zip-Loc™ bags and stored at 4° C.) The plates are washed with PBS/Tween™ 20 (0.5 ml Tween™ 20-Polysorbate surfactant/liter PBS) prior to use.

An antibody dilution buffer (0.15M NaCl, 0.5% bovine serum albumin, 0.05M $NaHPO_4$, pH 8.0, hereinafter referred to as ADB) is prepared and filter sterilized (0.22 micron cellulose acetate membranes). Test sera, and positive and negative control sera, are diluted with this buffer (40 ul serum in 360 ul buffer, or 1:10 v/v).

Diluted test sera, and positive and negative control sera (50 ul of each) are dispensed in duplicate to appropriate wells; 100 uls ADB are also dispensed into a few wells to serve as background. Fifty ul biotinylated monoclonal antibody prepared in the last example and dissolved in sterile ADB (500 ng/ml for MAb 290 and 1 ug for MAb 035) is added to each well except the background ADB controls. The plate is incubated for one hour at room temperature, and then washed three times with PBS/Tween 20.

Fifty ul of streptavidin-horseradish peroxidase (obtained from Zymed, Laboratories, Inc., South San Francisco, Calif.) dissolved in ADB (1:2000 dilution) is added to all the wells. The plate is incubated for 30 minutes at room temperature, and then washed three times with PBS/Tween™ 20. A peroxidase substrate solution is prepared immediately before use by combining 40 ul 2% $H_2O_2$ with 10 ml 0.08M ABTS in 0.1M citrate buffer, pH 4.0. One hundred ul of this substrate solution is added to all the wells.

The plate is incubated for 10 to 30 minutes, and 50 ul of a stop buffer (sterile 2% sodium dodecyl sulfate) quickly added to all the wells.

The plate is read at 410 nm. Readings from the plate background control wells are averaged and subtracted from the averages of readings from sample duplicates to yield adjusted sample averages. The adjusted sample averages are divided by the averaged value of the negative control sera. The values are multiplied by 100 to express the data as a percentage of the negative control.

If the results fall between 65 to 75%, samples should be rerun at different dilutions (e.g., 1:5, 1:10, or 1:15), or against a second BTV specific monoclonal antibody, or submitted to the National Veterinary Service Laboratory for better characterization.

EXAMPLE 3

This example describes a modified cELISA assay for detecting Bluetongue virus-specific antibodies in serum like that reported in Example 2 above, except that antigen is coated on plastic sticks attached to a microtiter plate lid instead of to the microtiter plate wells.

Antigen is allowed to bind to sticks on a 96-well plastic lid as described in Olsson, L., et al., *J. Immunol. Methods*, 61:17–32 (1983) at page 20. The lids are washed with Tween™ 20/PBS prior to use, and test sera, positive and negative control sera, background controls, and biotinylated monoclonal antibody are added to appropriate wells on the matching plate as described in the above Example. The procedure is then the same, except that the lid must be washed after the monoclonal and enzyme incubations, and either the plate must also be washed, or, preferably, different plates may be used for the monoclonal, the enzyme, and the substrate incubations, respectively.

EXAMPLE 4

This example also describes a modified cELISA assay for detecting Bluetongue virus-specific antibodies in serum like that reported in Example 2, except that magnetic beads are coated with antigen instead of a microtiter plate.

Magnetic polyacrylamide (4%)-agarose (4%) beads containing iron oxide (7 to 10%) are coated with the antigen of Example 1 as described by Guesdon, J.-L, and Avrameas, S., 14 *Immunochemistry* 443–447 (1977). The beads are added to a series of tubes, and diluted test sera, and positive and negative test sera are dispensed in duplicate to appropriate tubes; ADB is also dispensed to a few tubes to serve as background. Biotinylated monoclonal antibody prepared in Example 1 is added to each tube except the background ADB controls.

The tubes are rotated during an incubation and then washed on a magnetic rack with PBS/Tween™ 20. Streptavadin-horseradish peroxidase is added to each tube, the tubes are rotated during an incubation, and excess conjugate is removed by three washings with PBS/Tween™ 20. Peroxidase substrate is then added to each tube, then stop buffer after a short rotation/incubation, and color is read as described in Example 2.

EXAMPLE 5

In this example, a monoclonal antibody of Example 1 is conjugated directly with horseradish peroxidase as outlined in Ausubel, F. M., et al., eds., *Current Protocols in Molecular Biology*, John Wiley, New York, volume 2, supplement 10, (1990), Unit 11.1.2. This enzyme conjugated antibody is then used in an ELISA for detecting Bluetongue virus-specific antibodies in serum.

A 96-well microtiter plate is coated with the Example 1 antigen, washed prior to use, and incubated with test sera, positive and negative control sera, and ADB in various wells as described in Example 2. The plate is washed three times with PBS/Tween™ 20, and, instead of then incubating with biotinylated monoclonal antibody followed by streptavidin-horseradish peroxidase as set out in Example 2, the plate is incubated with the peroxidase-conjugated monoclonal for an hour at room temperature. The plate is washed three times with PBS/Tween™ 20, peroxidase substrate added, and incubation and reading carried out as described in Example 2.

EXAMPLE 6

This example describes a qualitative assay for detecting Bluetongue virus-specific antibodies in serum. This method involves a visual evaluation of peroxidase activity using any of the ELISAs described in Examples 2 through 5.

A weak positive control serum (in duplicate or triplicate) is included among the wells or tubes in the assay with the test sera, positive and negative control sera, and buffer background samples. After the stop buffer has terminated the enzyme reaction, instead of using a spectrophotometer, color development is assessed visually. The weak positive control provides a cut off point between uninfected and infected sera.

EXAMPLE 7

Instead of using microtiter plates or lids, or magnetic beads, the antigen of Example 1 may be bound to nitrocellulose paper (more fully described in Ausubel, cited above, Unit 10.8.1 (1987)). The assay may be employed for detecting Bluetongue virus-specific antibodies in serum using either the biotinylated monoclonal antibody of Example 1 with streptavidin-peroxidase, or the monoclonal-peroxidase of Example 5, following the protocols outlined above.

EXAMPLE 8

This example describes a shortened form of the cELISA described in Example 2.

The reagents and manipulations of Example 2 are followed, except that diluted sera, biotinylated monoclonal antibody, and streptavidin-horseradish peroxidase are incubated together in one step for 15 minutes to 1 hour at room temperature. The plate is washed, peroxidase substrate added, and the assay continued as described in Example 2.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims.

What is claimed is:

1. A hydridoma selected from the group consisting of A.T.C.C. accession number HB 10567 and A.T.C.C. accession number HB 10568 which secretes $IgG_{2a}$ monoclonal antibody which is group-specific to 24 serotypes of Bluetongue virus antigen.

2. A monoclonal antibody produced by a hybridoma of claim 1.

3. An antibody according to claim 2 which has been isolated and purified.

4. A hybridoma bearing A.T.C.C. accession number HB 10567.

5. An antibody produced by the hybridoma of claim 4.

6. An antibody according to claim 5 which has been isolated and purified.

7. A hybridoma bearing A.T.C.C. accession number HB 10568.

8. An antibody produced by the hybridoma of claim 7.

9. An antibody according to claim 8 which has been isolated and purified.

* * * * *